United States Patent [19]
Hui et al.

[11] Patent Number: 5,271,073
[45] Date of Patent: Dec. 14, 1993

[54] OPTICAL FIBER SENSOR AND METHOD OF MANUFACTURE

[75] Inventors: Henry K. Hui, Laguna Niguel; Terry J. Lumsden, San Marcos, both of Calif.

[73] Assignee: Puritan-Bennett Corporation, Carlsbad, Calif.

[21] Appl. No.: 565,639

[22] Filed: Aug. 10, 1990

[51] Int. Cl.⁵ .................. G02B 6/10; G01N 21/64
[52] U.S. Cl. ........................... 385/12; 427/163; 385/13
[58] Field of Search ............. 350/96.29, 96.30, 96.31, 350/96.33, 96.34; 427/163; 385/12, 13

[56] References Cited

U.S. PATENT DOCUMENTS

| | | | |
|---|---|---|---|
| Re. 31,879 | 5/1985 | Lübbers et al. | 436/133 |
| 4,200,110 | 4/1980 | Peterson et al. | 128/634 |
| 4,399,099 | 8/1983 | Buckles | 422/58 |
| 4,476,870 | 10/1984 | Peterson et al. | 128/634 |
| 4,560,248 | 12/1985 | Cramp et al. | 350/96.34 |
| 4,682,895 | 7/1987 | Costello | 356/402 |
| 4,752,115 | 6/1988 | Murray et al. | 350/96.29 |
| 4,842,783 | 6/1989 | Blaylock | 264/1.4 |
| 4,867,919 | 9/1989 | Yafuso et al. | 264/1.5 |
| 4,886,338 | 12/1989 | Yafuso ete al. | 350/96.29 |
| 4,906,106 | 3/1990 | Kaufmann et al. | 385/12 X |
| 4,906,249 | 3/1990 | Fogt et al. | 8/647 |
| 4,925,268 | 5/1990 | Iyer et al. | 350/96.29 |
| 4,954,318 | 9/1990 | Yafuso et al. | 350/96.29 X |
| 5,006,314 | 4/1991 | Gourley et al. | 350/96.29 X |

FOREIGN PATENT DOCUMENTS 106086  5/1974  German Democratic Rep. .
88/05533  7/1988  PCT Int'l Appl. .

Primary Examiner—Akm E. Ullah
Attorney, Agent, or Firm—Fulwider Patton Lee & Utecht

[57] ABSTRACT

The optical fiber sensor is formed from an optical fiber having a light conducting optical fiber core, and a coating of cladding material, with a length of a sensing material matrix applied to the distal portion of the optical fiber core. The method involves removing a length of the cladding material from the distal portion of the optical fiber to expose a distal tip of the optical fiber core, applying a sensing material matrix to the exposed distal portion of the optical fiber core, and applying a coating of reflective material over the sensing material matrix.

28 Claims, 1 Drawing Sheet

OPTICAL FIBER SENSOR AND METHOD OF MANUFACTURE

BACKGROUND OF THE INVENTION

1. Field of the Invention

This invention is generally directed to optical fiber sensors, and more specifically relates to an optical fiber sensor having a light conducting core and a coating of cladding material, with a length of a sensing material applied to the distal portion of the optical fiber core.

2. Description of Related Art

Measurement of concentrations of an analyte in a fluid mixture has become an important part of modern medicine. For example, it has been found that the concentration of oxygen in the blood can be measured from the property of certain dye indicators to fluoresce at particular wavelengths of light when irradiated by light of a specific wavelength range, and from the property of oxygen to quench this fluorescence. Intravascular catheters incorporating such dye indicators and optical fibers have been devised for monitoring blood oxygen levels, blood $CO_2$ levels and parameters such as pH.

Optical fibers are generally formed with an inner light conducting core and an outer light refracting or light reflecting cladding material. One previous approach to construction of an optical fiber sensor involves the attachment of a dye filled porous glass to the tip of the optical fiber, such as by an adhesive. However, this method allows the possibility of misalignment of the porous glass on the optical fiber, and the possibility of all or a portion of the porous glass becoming separated from the optical fiber due to mechanical perturbation. Another approach has involved the application of sensing material directly to the tip of the optical fiber, thereby adding to the radial dimension of the optical fiber tip. However, where such an optical fiber sensor is to be used for intravascular monitoring of blood oxygen levels, for example, it would be desirable for the sensor portion not to be larger than the optical fiber itself. Another approach has involved the attachment of a sleeve which contains the dye indicator sensing material in a matrix to the end of an optical fiber, such as by adhesive. However, this construction may also be dislodged due to mechanical perturbations, and entails a labor intensive manufacturing process.

From the above, it may be seen that the current methods of constructing optical fiber sensors which include sensor material distributed along the distal portion of the fiber are either labor intensive, fragile, present difficult quality control issues or some combination of these problems. Thus, there remains a need for an optical fiber sensor which may be more simply manufactured, such as by a dipping process, and which can provide good adhesion between the surface of the optical fiber core and the sensing material applied over it. It would also be desirable if the construction allowed control of the thickness of the sensor, and allowed formation of the sensor so as to conform to the shape and thickness of the optical fiber, to minimize mechanical perturbations, and to facilitate use of the sensor for intravascular monitoring of vital signs and parameters, such as blood oxygen levels.

SUMMARY OF THE INVENTION

Briefly and in general terms, an optical fiber sensor according to the present invention is formed by removing a portion of the cladding from an optical fiber to expose the core of the optical fiber, and applying a length of a sensing material matrix to the exposed optical fiber core, as by a dipping process.

In a presently preferred embodiment, the method of the invention generally involves making an optical fiber sensor from an optical fiber having a light conducting core, and a coating of cladding material thereover, by removing a length of said cladding material from the distal portion of the optical fiber to expose a distal tip of the core, applying a sensing material matrix to the exposed distal portion of the optical fiber core, and applying a coating of reflective material over the sensing material matrix.

In one currently preferred embodiment of the invention, the method for making the optical fiber sensor includes chemically treating the surface of the exposed distal portion of the fiber core with a primer to improve adhesion between the glass surface and the sensing material to be deposited.

In another currently preferred embodiment, the method of the invention involves dipping the exposed distal portion of the optical fiber core into an uncured liquid form of the sensing material matrix, and controlling the thickness of the layer of sensing material matrix by controlling the viscosity of the uncured liquid form of the sensing material matrix.

Other aspects and advantages of the invention will become apparent from the following detailed description, and the accompanying drawings which illustrate by way of example the features of the invention.

DETAILED DESCRIPTION OF THE PREFERRED EMBODIMENT

Figure 1:
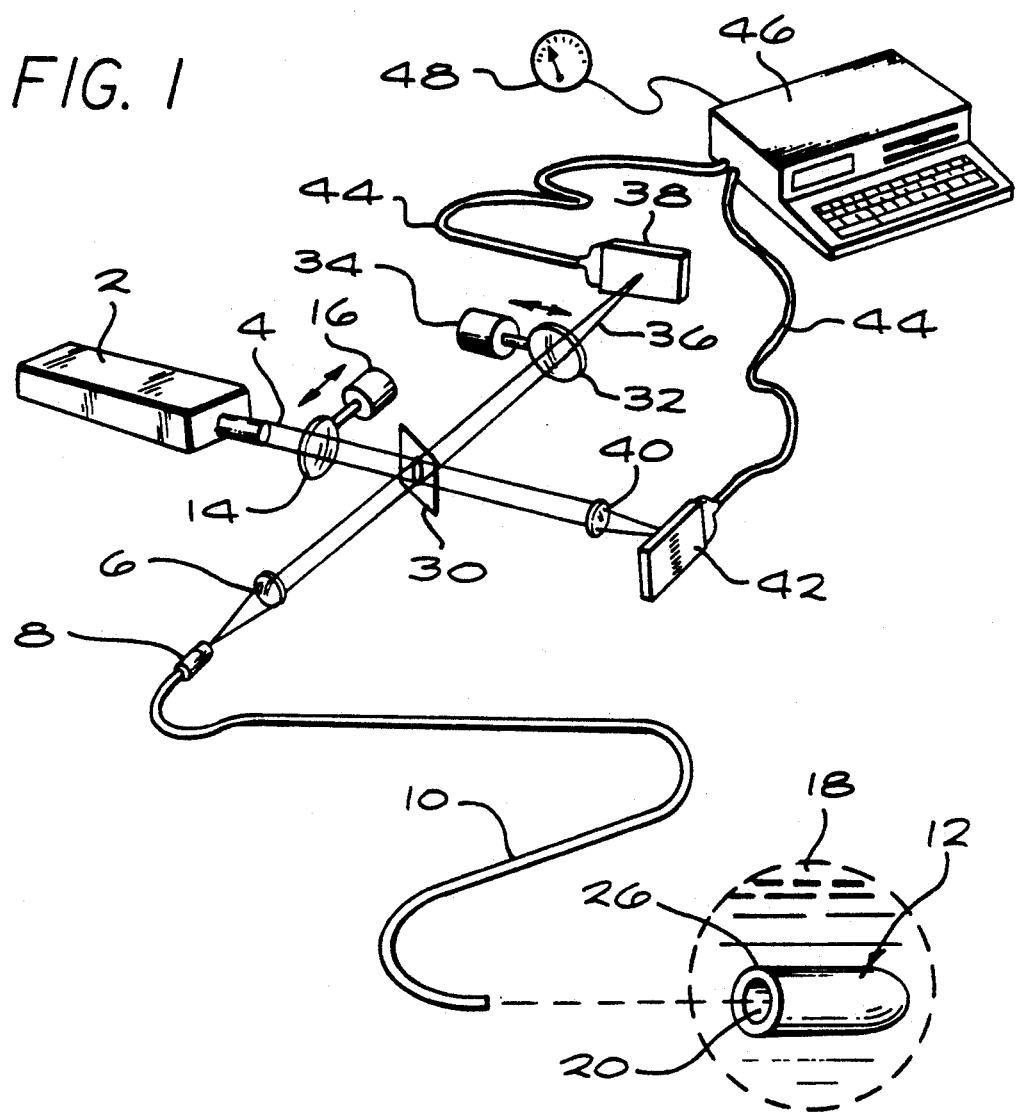
FIG. 1 is a perspective diagram of an optical fiber sensor system utilizing the sensor of the invention for monitoring blood oxygen levels

As is shown in the drawings which are provided for purposes of illustration and not by way of limitation, the invention is embodied in an optical fiber sensor apparatus and a method for making the sensor apparatus. The optical fiber sensor apparatus of the invention may be utilized, for example, in a system for monitoring blood oxygen levels, although other parameters may be measured utilizing optical fiber systems incorporating the invention. As is illustrated in FIG. 1, in such a system a light source 2 provides a collimated output light beam 4 that is passed through a dichroic mirror 30 and focused by a lens system 6 into a connector 8 of an optical fiber 10, which carries the light beam to a sensor module 12 at a distal end of the optical fiber. The light source preferably includes one or more excitation filters 14, actuated and controlled by stepper motor 16, for controlling the wavelength range of the light provided to the sensor module. Sensor module 12 is adapted to be placed in a fluid 18, such as blood, for quantitative measurement of a chemical parameter of the fluid. While the present description is directed to the measurement of oxygen, the sensor could, of course, be adapted to detect concentrations of other gases, such as carbon dioxide, as well as pH, or other blood chemistry or constituents. The arrangement of FIG. 1 is included for the purpose of generally illustrating the type of system in which the invention may be used, but those skilled in the art will recognize that a variety of optical systems and arrangements for activating and readout subsystems may be used.

The output optical fiber 10 may also carry light fluoresced from the dye indicators via the dichroic mirror 30 to emission filters 32 which may be actuated by stepper motor 34 and direct the fluorescent light beam 36 upon a detector array 38. Similarly, the portion of the light beam 4 that passes through the dichroic mirror 30 may be focused by a suitable lens 40 upon a reference detector array 42, which allows measurement of the excitation signal strength. The electrical output of the detectors is fed through cables 44 to a computer 46, such as an IBM PC, which receives the electrical output of the detectors and determines the blood analyte being monitored, such as $O_2$. The computer is preferably programmed to determine the $O_2$ based upon the specific measurement of fluorescence intensity represented by the electrical output signal received by the computer, according to an algorithm based upon signal outputs from measurements from samples with known $O_2$ levels. The output of the computer may be indicated on a meter 48 or another suitable readout device.

Figure 2:
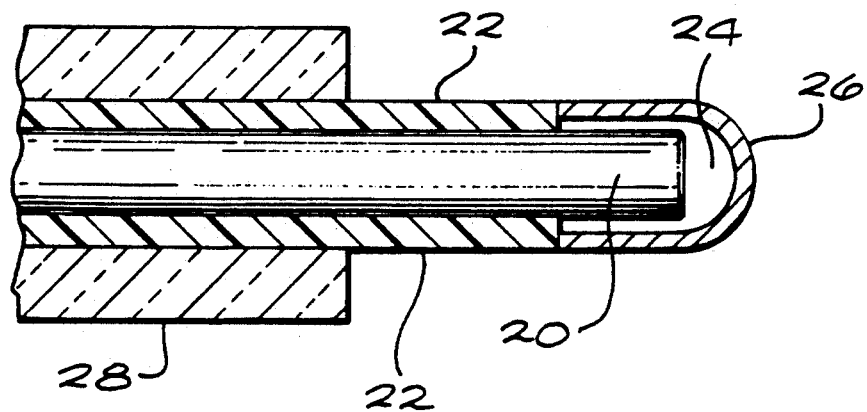
FIG. 2 is an enlarged, cross-sectional schematic diagram of the optical fiber sensor.

As is illustrated in FIG. 2, the optical fiber sensor module 12 is generally formed from an optical fiber having an inner light conducting core 20 and an outer cladding material 22 having a refractive index such that light conducted by the core is substantially retained in the core material. A length of cladding on the distal end of the optical fiber is removed, leaving an exposed distal tip of the core which is coated with a polymeric sensing material matrix 24, which is typically silicone, and more specifically may be polydimethylsiloxane, polydimethyldiphenylsiloxane, or cross-linked derivatives or copolymers thereof. The sensing matrix preferably contains one or more dye indicators, such as coronene, decacyclene, perylene, or the like which are known to fluoresce in response to irradiation with light of various wavelength ranges. A coat of reflective material 26 is also preferably provided over the dye containing sensing matrix, to retain and reflect both the irradiating light and the fluorescence emissions from the dye indicators of the sensing material matrix. For use as an intravascular optical fiber sensor apparatus, the shaft of the optical fiber may also be coated with a material 28 such as TEFLON or TEFZEL.

A method of making the optical fiber sensor according to the present invention involves removing a length of the cladding material from the distal portion of the optical fiber to expose the distal tip of the optical fiber core. The cladding is currently preferably removed by an electrical discharge across the distal tip of the optical fiber sufficient to vaporize the cladding material, although the cladding material may also be removed by other means, such as by chemical solvents, pyrolysis, or possibly appropriate mechanical methods. The length of cladding material removed from the distal tip of the fiber in order to expose a distal portion of the optical fiber core is preferably approximately 0.5 mm, although the length may range from approximately 10 microns to 100 millimeters. The thickness of cladding material removed is typically approximately 15 microns/side.

After the cladding material is removed from the tip of the optical fiber, the exposed distal portion of the core, which is typically glass, is cleaned and chemically treated to improve wetability of the glass core. In a currently preferred cleaning and treatment procedure, the exposed fiber core is washed with a solvent such as isopropanol, dried, and treated with concentrated sulfuric acid. Thereafter the exposed fiber core is rinsed with water, and treated with a primer to improve adhesion between the glass surface and the sensing material. The specific primer selected will depend upon the chemical characteristics of the sensing material matrix. Currently, the preferred sensing material matrix is a silicone matrix, and the preferred primer is vinyltrichlorosilane for an $O_2$ sensor. In a preferred embodiment adaptable to the measurement of blood pH levels, isocyanatotriethoxysilane may advantageously be utilized as a primer.

Thereafter, the exposed distal portion of the fiber core is again rinsed with isopropanol, and the sensing material is applied by dipping the exposed distal portion of the optical fiber core into an uncured, liquified silicone matrix material containing the dye indicator material. The dipping process may be automated for mass production of the optical fiber sensors. By controlling the viscosity of the uncured silicone matrix material, a desired thickness of matrix material may be applied. The thickness of the layer of sensing material applied at the extreme tip of the fiber optic core is preferably about 55 microns, although this may range approximately from 5 to 250 microns. The radial thickness of the material along the sides of the exposed fiber core using this method is typically 7.5 microns, although this typically may range from approximately 1 to 20 microns. The sensing material matrix is then allowed to cure, either by heat or by a chemical curing agent, or both. After the sensing matrix has solidified, a coating of a reflective material may be applied over the sensing matrix to provide protection, optical isolation and reflection of both the excitation and fluorescence emission light. The amount of this reflective coating material is preferably approximately 55 microns thick at the extreme distal tip of the fiber core, and approximately 7.5 microns thick along the sides of the optical fiber core.

From the above, it will be apparent to those skilled in the art that the method and apparatus of the present invention represents an important improvement over previous methods and apparatus for the construction of distributed sensors at the distal tip of an optical fiber based intravascular blood sensor. In particular, the present invention provides important advantages in quality, reproducability and economy of construction for such sensors, as well as reducing the size and complexity of the sensor chemistry located on the fiber.

It will also be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method of making an optical fiber sensor from an optical fiber having proximal and distal portions, a light conducting optical fiber core with a side portion and a coating of cladding material over said side portion, the steps of the method comprising:

removing a length of said cladding material from the distal portion of the side portion of the optical fiber to expose a distal side portion of the optical fiber core;

applying a polymeric, semipermeable sensing material matrix containing a dye indicator material to the exposed distal portion of the optical fiber core; and applying a coating of reflective material over the sensing material matrix.

2. The method of claim 1, wherein said cladding material is removed by electrical discharge.

3. The method of claim 1, wherein the length of cladding material removed ranges from approximately 10 microns of 100 mm.

4. The method of claim 1, wherein said optical fiber core is made of glass, and said step of removing a length of said cladding material further comprises cleaning the surface of the exposed distal portion of the optical fiber core and treating the surface with sulfuric acid to improve wettability of the exposed optical fiber core.

5. The method of claim 4, wherein said step of applying said sensing material matrix includes chemically treating the surface of the exposed distal portion with a primer to improve adhesion between the surface and the polymeric, semipermeable sensing material matrix.

6. The method of claim 5, wherein said primer comprises vinyltrichlorosilane.

7. The method of claim 1, wherein the sensing material matrix comprises a polymeric silicone.

8. The method of claim 1, wherein said matrix comprises cross-linked polydimethylsiloxane.

9. The method of claim 9, wherein said step of applying the sensing material matrix comprises dipping the exposed distal portion of the optical fiber core into an uncured liquid form of the sensing material matrix.

10. The method of claim 9, wherein said step of applying the sensing material matrix comprises controlling the thickness of the sensing material matrix by controlling the viscosity of the uncured liquid form of the sensing material matrix.

11. The method of claim 1, wherein the applied thickness of said sensing material matrix ranges approximately from 1 to 20 microns along the sides of the optical fiber core and ranges approximately from 5 to 100 microns at the extreme distal tip of the optical fiber core.

12. The method of claim 9, further comprising the step of curing said uncured liquid form of the sensing material matrix.

13. An optical fiber sensor apparatus comprising:
an optical fiber having proximal and distal portions, a light conducting optical fiber core with a side portion having a coating of cladding material over the proximal portion of the side portion of said optical fiber core and with said coating of cladding material having been removed from the distal portion of the side portion of said optical fiber core; and
a length of a polymeric, semipermeable sensing material matrix containing a dye indicator material applied to the uncladded distal portion of the optical fiber core.

14. The apparatus of claim 13, further including a coating of reflective material applied over the sensing material matrix.

15. The apparatus of claim 13, wherein the sensing material matrix is a polymeric silicone matrix.

16. The apparatus of claim 13, wherein said matrix comprises cross-linked polydimethylsiloxane.

17. The apparatus of claim 13, wherein the applied thickness of said sensing material matrix ranges approximately from 1 to 20 microns along the sides of the optical fiber core and ranges approximately from 5 to 100 microns at the extreme distal tip of the optical fiber core.

18. A method of making an optical fiber sensor from an optical fiber having an optical fiber core and a side surface coated with a cladding material, the steps of the method comprising:
removing a portion of said cladding material from the side surface of the optical fiber to expose a portion of the side surface of the optical fiber core;
applying a polymeric, semipermeable sensing material matrix containing a dye indicator material to the exposed portion of the optical fiber core; and
applying a coating of reflective material over the sensing material matrix.

19. The method of claim 18, wherein said optical fiber core is made of glass, the optical fiber core has a distal surface portion which is exposed by said removal of cladding material, and said step of removing said cladding material further comprises cleaning the exposed distal surface portion of the optical fiber core and treating the surface with acid to improve wettability of the exposed optical fiber core.

20. The method of claim 18, wherein said polymeric, semipermeable sensing matrix is applied in an uncured liquid form, and said step of applying the sensing material matrix comprises controlling the thickness of the sensing material matrix by controlling the viscosity of the uncured liquid form of the sensing material matrix.

21. An optical fiber sensor apparatus comprising:
a optical fiber having a light conducting optical fiber core with a side surface substantially coated with a cladding material and a portion of said side surface having said cladding material removed therefrom to provide an uncladded side surface portion of said optical fiber; and
a polymeric, semipermeable sensing material matrix containing a dye indicator material applied to the uncladded side surface portion of the optical fiber core.

22. The apparatus of claim 21, further including a coating of reflective material applied over the polymeric, semipermeable sensing material matrix.

23. The apparatus of claim 21, wherein the polymeric, semipermeable sensing material matrix comprises a polymeric silicone matrix.

24. The apparatus of claim 21, wherein said matrix comprises cross-linked polydimethylsiloxane.

25. A method of making an optical fiber sensor from an optical fiber having proximal and distal portions, a glass light conducting optical fiber core with a side portion and a coating of cladding material over said side portion, the steps of the method comprising:
removing a length of said cladding material from the distal portion of the side portion of the optical fiber to expose a distal side portion of the optical fiber core;
cleaning the surface of the exposed distal portion of the optical fiber core and treating the surface with sulfuric acid to improve wettability of the exposed optical fiber core; and
applying a polymeric, semipermeable sensing material matrix containing a dye indicator material to the exposed distal potion of the optical fiber core.

26. The method of claim 25, wherein said step of applying said sensing matrix includes chemically treating the surface of the exposed distal portion with a primer to improve adhesion between the surface and the polymeric, semipermeable sensing material matrix.

27. The method of claim 26, wherein said primer comprises vinyltrichlorosilane.

28. A method of making an optical fiber sensor from an optical fiber having proximal and distal portions, a light conducting optical fiber core with a side portion and a coating of cladding material over said side portion, the steps of the method comprising:

removing a length of said cladding material from the distal portion of the side portion of the optical fiber to expose a distal side portion of the optical fiber core; and applying a polymeric, semipermeable sensing material matrix containing a dye indicator material to the exposed distal portion of the optical fiber core by dipping the exposed distal portion of the optical fiber core into an uncured liquid form of the sensing material matrix, and controlling the thickness of the sensing material matrix by controlling the viscosity of the uncured liquid form of the sensing material matrix.

* * * * *